(12) United States Patent
Lavallee et al.

(10) Patent No.: US 8,231,631 B2
(45) Date of Patent: Jul. 31, 2012

(54) DISTRACTOR SYSTEM

(75) Inventors: Stephane Lavallee, Saint Martin d'Uriage (FR); Christopher Plaskos, New York, NY (US)

(73) Assignee: Perception Raisonnement Action en Medecine, La Tronche (FR)

( * ) Notice: Subject to any disclaimer, the term of this patent is extended or adjusted under 35 U.S.C. 154(b) by 1548 days.

(21) Appl. No.: 11/422,832

(22) Filed: Jun. 7, 2006

(65) Prior Publication Data
US 2007/0233144 A1 Oct. 4, 2007

Related U.S. Application Data

(60) Provisional application No. 60/784,343, filed on Mar. 20, 2006.

(51) Int. Cl.
*A61B 17/58* (2006.01)

(52) U.S. Cl. ......................................................... 606/90

(58) Field of Classification Search .................. 606/90, 606/86 R, 87–89, 105; 623/17.12, 20.14–20.36, 623/403
See application file for complete search history.

(56) References Cited

U.S. PATENT DOCUMENTS

| | | | |
|---|---|---|---|
| 4,501,266 A | 2/1985 | McDaniel | |
| 4,521,998 A * | 6/1985 | DeLorme | 52/81.3 |
| 5,176,683 A * | 1/1993 | Kimsey et al. | 606/86 R |
| 5,390,683 A * | 2/1995 | Pisharodi | 128/898 |
| 5,540,696 A | 7/1996 | Booth, Jr. et al. | |
| 5,597,379 A | 1/1997 | Haines et al. | |
| 5,733,292 A * | 3/1998 | Gustilo et al. | 606/88 |
| 5,800,438 A | 9/1998 | Tuke et al. | |
| 5,860,980 A | 1/1999 | Axelson, Jr. et al. | |
| 5,911,723 A | 6/1999 | Ashby et al. | |
| 6,022,377 A | 2/2000 | Nuelle et al. | |
| 6,126,689 A * | 10/2000 | Brett | 623/17.16 |
| 6,231,712 B1 * | 5/2001 | Torres | 156/204 |
| 6,231,716 B1 * | 5/2001 | White et al. | 156/345.54 |
| 6,232,347 B1 * | 5/2001 | Mendel et al. | 514/646 |
| 6,375,682 B1 * | 4/2002 | Fleischmann et al. | 623/17.12 |
| 6,482,209 B1 * | 11/2002 | Engh et al. | 606/79 |
| 6,575,980 B1 | 6/2003 | Robie et al. | |
| 6,875,235 B2 * | 4/2005 | Ferree | 623/20.32 |
| 7,083,650 B2 * | 8/2006 | Moskowitz et al. | 623/17.11 |
| 7,309,363 B2 * | 12/2007 | Dietz | 623/23.47 |
| 7,314,487 B2 * | 1/2008 | Ralph et al. | 623/17.13 |
| 7,621,950 B1 * | 11/2009 | Globerman et al. | 623/17.11 |
| 2003/0187452 A1 | 10/2003 | Smith et al. | |
| 2003/0236520 A1 * | 12/2003 | Lim et al. | 606/61 |
| 2005/0267485 A1 | 12/2005 | Cordes | |
| 2006/0149277 A1 * | 7/2006 | Cinquin et al. | 606/90 |
| 2006/0235423 A1 * | 10/2006 | Cantu | 606/90 |
| 2007/0219561 A1 * | 9/2007 | Lavallee et al. | 606/90 |

FOREIGN PATENT DOCUMENTS

CA 2469555 A1 * 12/2002
WO WO 2004078047 A1 * 9/2004

* cited by examiner

*Primary Examiner* — Kevin T Truong
*Assistant Examiner* — Christopher Beccia
(74) *Attorney, Agent, or Firm* — Kim Krizman LLC

(57) ABSTRACT

A medical instrument includes a base; an upper member; and a linkage mechanism coupled to the base and the upper member and being operable to maintain the upper member in a variable fixed position that is substantially parallel to the base and spaced a predetermined, variable distance therefrom, wherein the linkage mechanism includes at least three linkage elements that are arranged at angles relative to one another such that when one link element opens, the other link elements open with at an equal angle resulting in the upper member being constrained to remain parallel to the base.

16 Claims, 4 Drawing Sheets

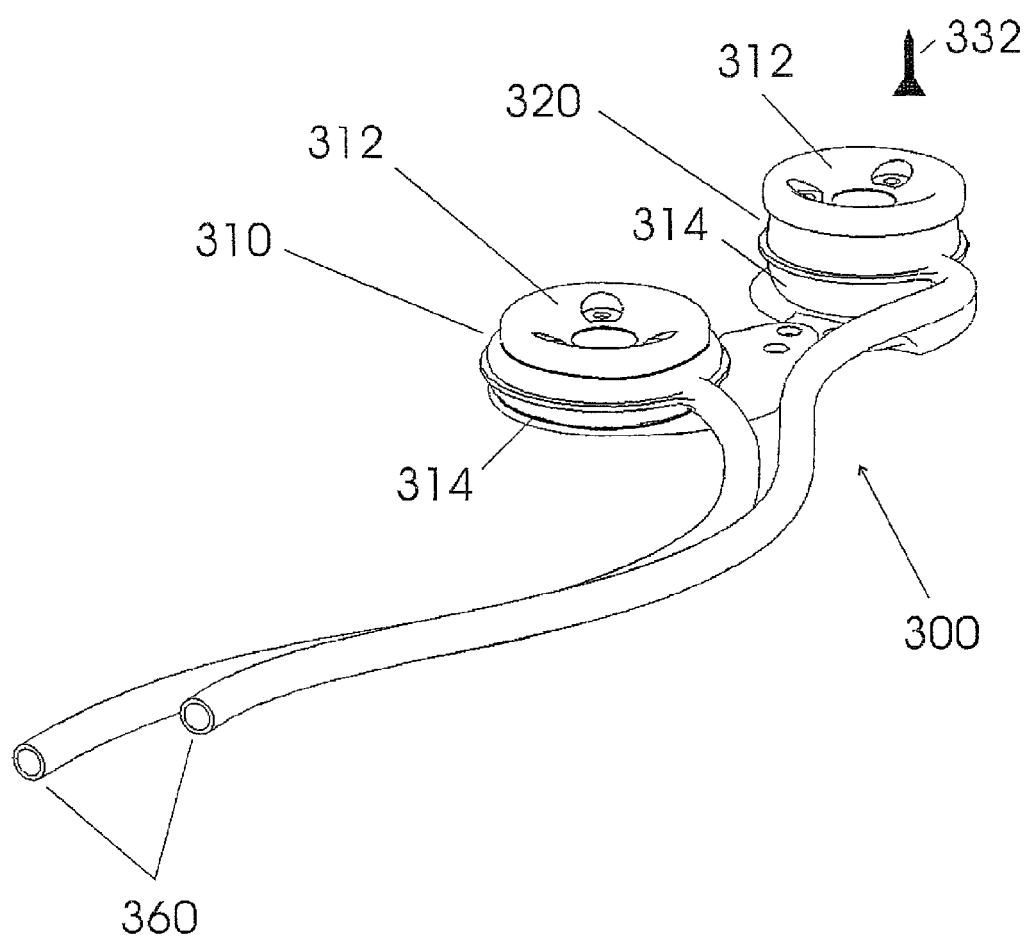

DISTRACTOR SYSTEM

CROSS-REFERENCE TO RELATED APPLICATION

The present application claims the benefit of U.S. patent application Ser. No. 60/784,343, filed Mar. 20, 2006, which is hereby incorporated by reference in its entirety.

TECHNICAL FIELD

The present invention relates to the field of joint replacement or joint resurfacing surgery, and more particularly, to a distractor (distraction device) that is used in a prosthesis implantation operation, such as a knee prosthesis implantation.

BACKGROUND

The success of joint replacement surgery is primarily dependent on two factors, namely, (1) the position of the implant components with respect to the boney anatomy; and (2) the postoperative state of the surrounding soft tissues. Joints are surrounded by ligamenteous and capsular tissue. The state of these soft tissues determines the laxity and stability of the joint. The state of the soft tissues is effected by the following two factors: (1) the position of the components; and (2) the amount of soft tissue releases performed by the surgeon, as discusses in U.S. patent application publication No. 2005/0267485, which is hereby incorporated by reference in its entirety. In addition, a number of devices and techniques have been described that attempt to facilitate ligament balancing during a TKA procedure and in particular, some of these techniques involve trial prosthesis components which are used after femoral and tibial bone cuts are made to assess ligament tissue. See, U.S. Pat. No. 5,733,292, which is hereby incorporated by reference in its entirety.

Other devices are used to measure a gap between the distal femur and proximal tibia in extension and to help a surgeon recreate that same gap when the distal femur and proximal tibia in extension to help a surgeon recreate that same gap when the knee is in flexion. See, U.S. patent application publication No. 2003/0187452 and U.S. Pat. No. 6,575,980, both of which describe "gap checking" devices, each of which is hereby incorporated by reference in its entirety. Other devices have been developed to help measure an amount of ligament tension or to apply a desired amount of tension to the ligaments and in addition, paddle-like devices have been suggested for applying or measuring tension across a knee joint. See, U.S. Pat. Nos. 4,501,266; 5,597,379; 5,540, 696; 5,800,438; 5,860,980; 5,911,723; and 6,022,377, each of which is hereby incorporated by reference in its entirety.

The device described in the above mentioned '485 publication is designed to determine the rotational alignment of the femoral component such that the knee is in optional tension; however, there are a number of disadvantages and limitations associated with this device. For example, the following are disadvantages associated with this device: (1) the distal femoral cut must be made first before the device is inserted and therefore, one can not change the planning in varus/valgus; proximal/distal, and flexion/extension; (2) the device must be fixed to the femur and therefore, requires bone screws on the medial and lateral sides which add invasiveness to the bone, as well as the soft tissues since access is required to the lateral side of the joint; (3) a vast number of components sizes for the tibia and the femur are still required; and (4) the system has constraints due to it not being able to account for different prosthetic designs using the same components, for example, different degrees of constraint or concavities of the tibial or femoral components.

SUMMARY

A medical instrument includes a base; an upper member; and a linkage mechanism coupled to the base and the upper member and being operable to maintain the upper member in a variable fixed position that is substantially parallel to the base and spaced a predetermined, variable distance therefrom, wherein the linkage mechanism includes at least three linkage elements that are arranged at angles relative to one another such that when one link element opens, the other link elements open with at an equal angle resulting in the upper member being constrained to remain parallel to the base.

In one embodiment, the instrument is a distraction device and it is intended for use in implant surgery, such as knee joint replacement, and there are two upper parts constructed to support condyles of the femur.

In one aspect, the base includes a first base plate and a second base plate that is pivotably coupled to the first base plate, wherein at least a portion of the first and second base plates lie in the same plane and is intended to be mounted to a planar surface, such as a tibial cut. The instrument further includes a controller operably coupled to the linkage mechanism to cause the controlled movement thereof resulting in movement of the upper part relative to the base. The controller is operably connected to an adjustable spacer element that has a body disposed around the linkage mechanism, with the body being fluidly connected to a fluid source such that controlled delivery of fluid to the body results in expansion of the spacer element and a distance between the upper part and base increasing. In one embodiment, the body of the spacer element is in the form of an expandable pouch that has a hollow interior in which the linkage mechanism is disposed, with the pouch being secured to the upper part and the base by means of fastening elements.

Other features and advantages of the present invention will be apparent from the following detailed description when read in conjunction with the accompanying drawings.

BRIEF DESCRIPTION OF THE DRAWINGS FIGURES

The foregoing and other features of the present invention will be more readily apparent from the following detailed description and drawings figures of illustrative embodiments of the invention in which:

FIG. 4 is a perspective view of one exemplary spacer means for changing the position of the distraction device of FIG. 2.

DETAILED DESCRIPTION OF PREFERRED EMBODIMENTS

FIGS. 1-4 illustrate a distraction device (distractor) 100 according to one exemplary embodiment of the present invention. The distraction device 100 is compatible with minimally invasive procedures, where the patella is not reflected (or reduced) and the knee joint is not opened completely.

Figure 1:
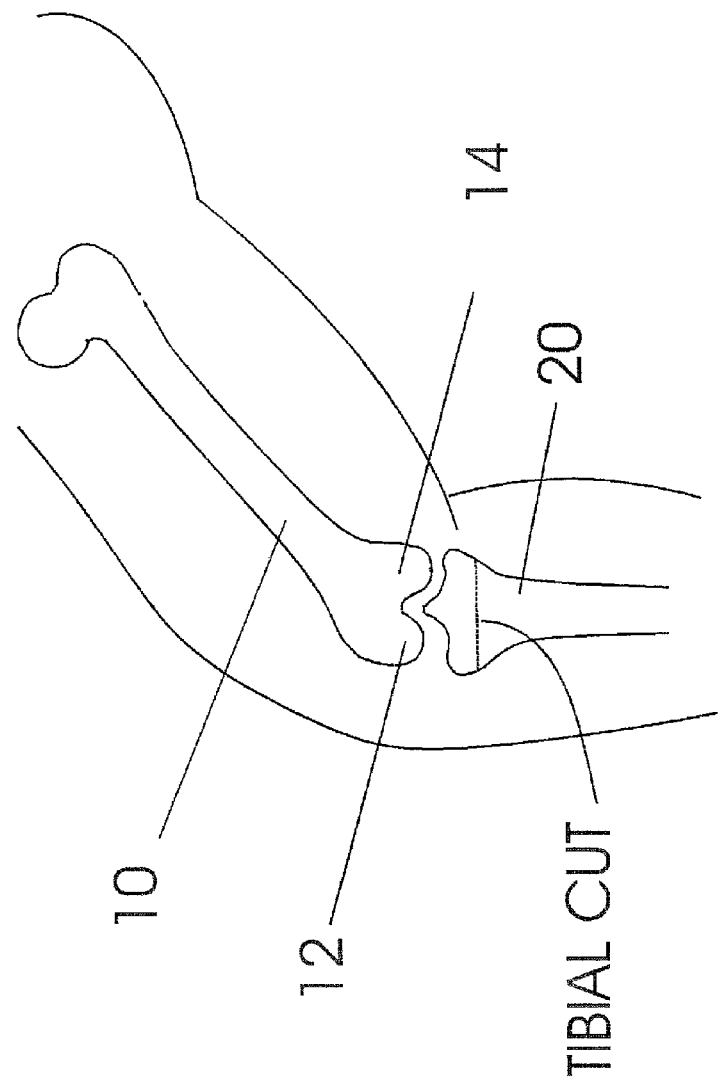
FIG. 1 is a side view of a knee joint defined by a femur bone and a tibia bone.

The distraction device 100 has a flat/planar base 110 which is configured and intended to rest or sit on a plateau cut that is made in a bone as part of the implant surgery. For purposes of illustration only, the distraction device 100 will be described as being used in a knee implant operation and thus FIG. 1 shows a femur bone 10 and tibia bone 20; however, the potential applications of the distraction device 100 extend and go beyond the knee implant surgery and thus, the following description of the application of the distraction device 100 in knee implant surgery is merely exemplary and not limiting of the present invention. In the case where the distraction device 100 is used in knee implant surgery, the base 110 thereof rests on a tibial plateau cut that is made near the end of the tibia 20.

Figure 2:
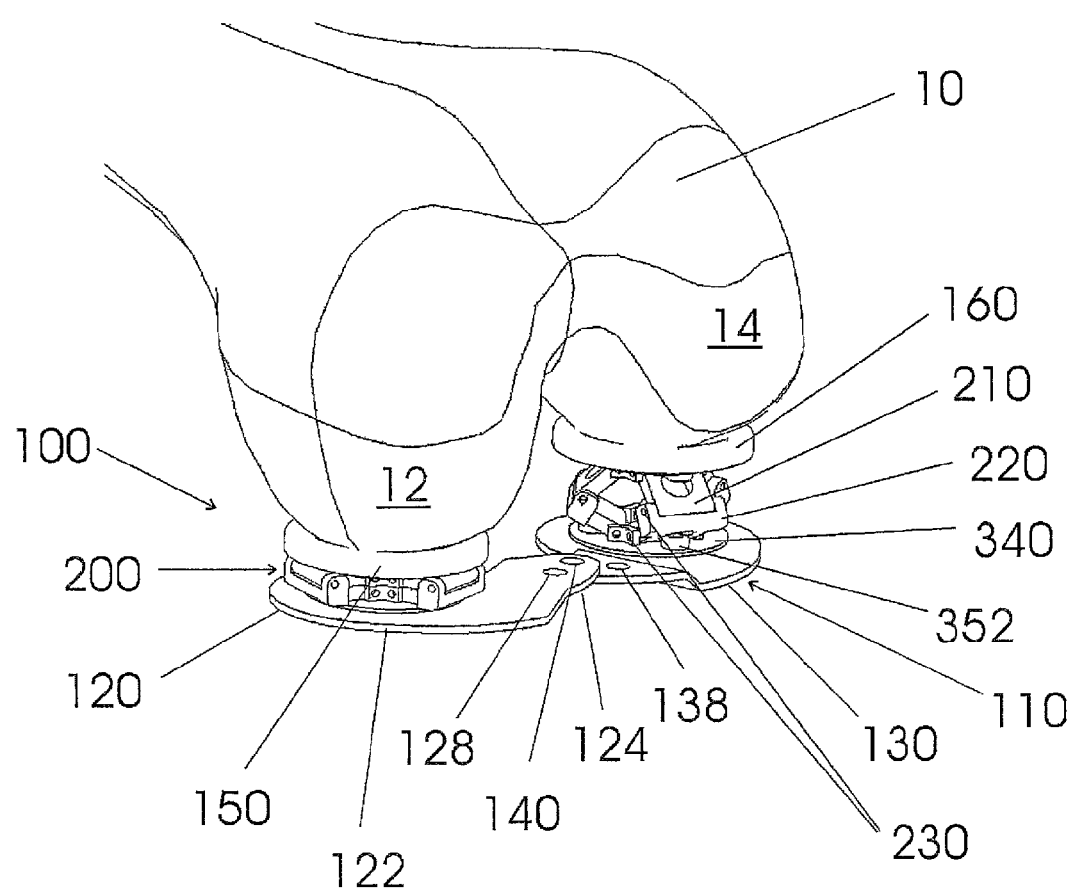
FIG. 2 is a perspective view a distraction device according to one embodiment relative to the femur bone.
Figure 3:
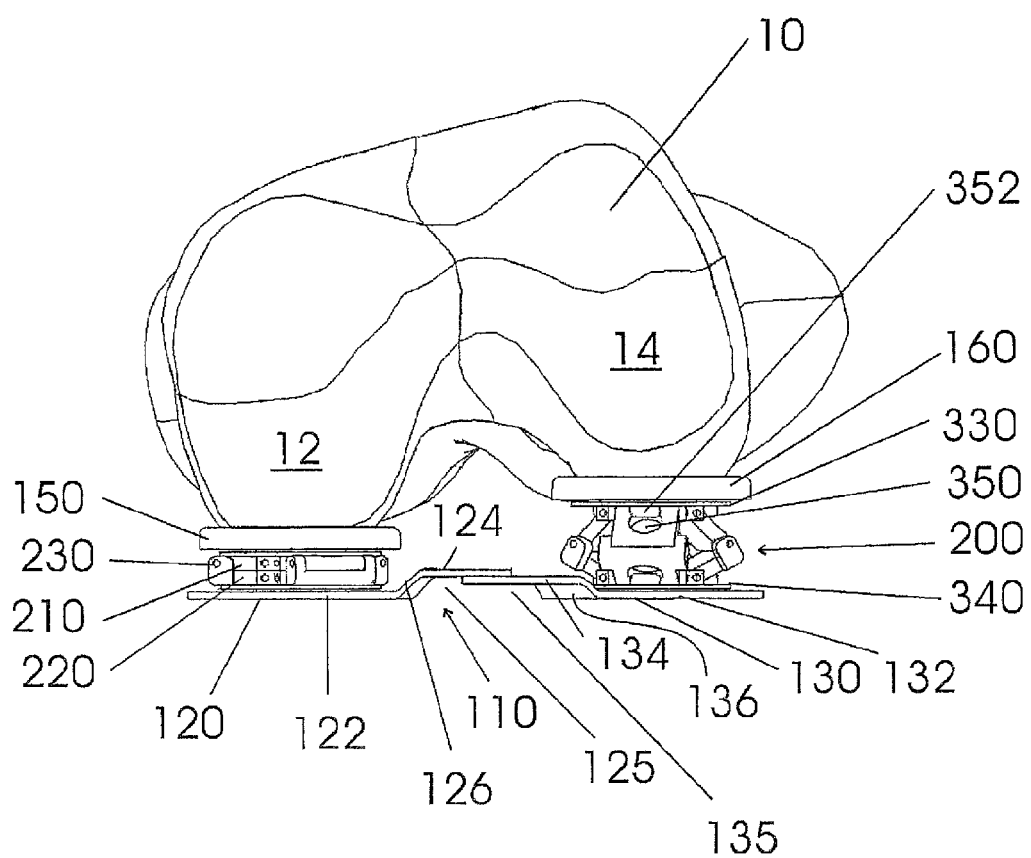
FIG. 3 is a side perspective view of the distraction device of FIG. 2.

The base 110 is configured so that it is adjustable to accommodate a range of knee sizes. More particularly, the base 110 is in the form of a plate and more specifically, the base 110 is informed of two base plates, namely, a first plate 120 (internal plate) and a second plate 130 (external plate). The first and second plates 120, 130 are adjustable relative to one another and in particular, the first and second plates 120, 130 are pivotably connected to one another by a pivot joint 140. In order for the first and second plates 120, 130 to lie in the same plane and be pivotally connected, the first plate 120 has a main portion 122 and a raised portion 124 that is connected to the main portion 122 by means of a ramp 126. As illustrated in FIG. 2, when the lower surface of the main portion 122 rests on the ground, the portion 124 is elevated relative to the ground such that a space 125 is formed under the lower surface of the raised portion 124. Similarly, the second plate 130 has a main portion 132 and a raised portion 134 that is connected to the main portion 132 by means of a ramp 136. As illustrated in FIG. 2, when the lower surface of the main portion 132 rests on the ground, the portion 134 is elevated relative to the ground such that a space 135 is formed under the lower surface of the raised portion 124.

The first and second plates 120, 130 are pivotally connected at the raised portions 124, 134 and as shown in FIG. 2, one raised portion (e.g., portion 124) overlies the other raised portion (e.g., portion 134). The pivot joint 140 extends through both of the raised portions 124, 134 and permits the two plates 120, 130 to pivot at the raised portions 124, 134 thereof. The raised portion 124 of the first plate 120 has an opening 128 formed therethrough proximate the pivot joint 140. Similarly, the raised portion 134 includes an opening or slot 138 proximate the pivot joint 140. A U-shaped piece (not shown) can be inserted into opening 128 and slot 138. By turning a nut (not shown) or the like that is part of a threaded post of the U-shaped piece that traverses the slot 138, the size and arrangement of the base 110, and in particular, the relative positions of the first and second plates 120, 130 can be locked into a fixed position. Since the portions 124, 134 are raised relative to the main portions 122, 132, respectively, receiving an object (e.g., the U-shaped piece) through the opening 128 and slot 138 does not interfere with the main portions 122, 132 resting on the planar cut since it can be received in the space 125, 135.

The lower surfaces of the first and second base plates 120, 130 can be rough or can have protrusions, such as spikes, so as to prevent the distraction device 100 from sliding around on the tibial plateau cut. In addition, openings can also be included so that the surgeon can fix the distraction device 100 to the tibial bone (at tibial cut) by means of pins or screws that are received through openings formed through the first and second plates 120, 130.

The distraction device 100 includes two upper femoral plateaus, namely, a first upper femoral plateau member 150 (internal) and a second upper femoral plateau member 160 (external). The first upper femoral plateau member 150 is configured and intended to support the internal (medial) condyle 12 of the femur 10, while the second upper femoral plateau member 160 is configured and intended to support the external (lateral) condyle 14 of the femur 10.

As described above in more detail and based on the pivoting action between the plates 120, 130, the distance of separation between each plateau members 150, 160 is adjustable. More specifically, the optimal distance of separation between the plateau members 150, 160 can be automatically computed from the femoral bone model, by for example, calculating the distance between the most posterior or most distal points on the femoral condyles 12, 14. An average of these two distances can be selected so that the distraction device 100 fits the femur 10 when the knee is in both flexion and in extension. Markings can be incorporated onto the distraction device 100, for example, on the base 110 (plates 120, 130) to indicate the separation distance so that the surgeon can adjust the tibial base distance to the appropriate value as determined by various techniques. Alternatively, a caliper system or similar tool can be used to measure the distance between the plateau members 150, 160. Alternatively, pair of holes can be made in the base plates 120, 130 of the distraction device 100 corresponding to predefined discrete distance that correspond to various sizes of a knee implant. The surgeon can then easily insert a peg or the like into the proper holes in order to replicate a particular size of the implant that corresponds to the planned implant size.

An upper surface of each of the first and second femoral plateau members 150, 160 is constructed to support and complement the respective condyle and can be convex in form in both the sagittal and frontal planes to better fit with the femoral condyles 12, 14, respectively. Thus, they can be spherical or they can have different curvatures in the different planes to simulate different levels of constraints.

The first and second upper femoral plateau members 150, 160 are coupled to the first and second base plates 120, 130, respectively, by means of a linkage mechanism 200 that ensures that each of the plateau members 150, 160 remains parallel to the respective lower base plate 120, 130 throughout the course of the distraction motion (i.e., the range of motion of a distraction operation).

The linkage mechanism 200 is formed of a plurality of link pairs 210, 220 connected to each other and coupled to one of the femoral plateau members 150, 160 and the respective base plate 120, 130 by pins or the like 230. As shown, the link 210 is connected at one end to one of the femoral plateau members 150, 160 and is connected at its other end to one end of the other link 220. The pins 230 permit pivoting of the links 210, 220 with respect to each other and with respect to the femoral plateau plates 150, 160 and the base plates 120, 130.

The links 210, 220 are arranged at angles to each other such that when one pair of links 210, 220 hinges or pivots open, all other link pairs 210, 220 open at an equal angle, thereby constraining the first and second upper femoral plateau members 150, 160 to remain parallel to the first and second lower base plates 120, 130.

In one exemplary embodiment, at least three linkage mechanisms 200 for each of the first and second femoral plateau members 150, 160 and the respective base plate 120, 130 are chosen to optimize the stability, strength and size of the linkage mechanism 200. However, it will be appreciated that each mechanism 200 can have more or less than three pairs of links 210, 220. Thus, two or four pairs of links 210, 220 can be used.

It will also be appreciated that instead of having link pairs defined by parts 210, 220 that are coupled to and between the first and second femoral plateau members 150, 160 and the respective base plate 120, 130, there can be more than two links in each set. In other words, link triplets defined by three link members pivotally attached to one another and to the first and second femoral plateau members 150, 160 and the respective base plate 120, 130 can be provided or link quadruplet defined by four link members can be employed instead of the illustrated link pairs 210, 220. The illustrated linkage mechanism 200 has been designed such that it has a low profile height on the order of about 5 mm when fully retracted as illustrated in FIG. 2, and a considerably higher height of about 15 mm or 20 mm when fully extended. If additional heights are required beyond the maximum height range, spacer blocks can be fastened onto the first and second upper femoral plateau members to augment the maximum achievable height.

The fastening mechanism that is incorporated into the distraction device 100 can be any number of different types, including but not limited to, a quick-clip or snap type mechanism, or a peg and hole type mechanism, or a sliding dove tail joint arrangement, etc. In addition, in the case where the above mentioned spacer blocks are used, these blocks can have similar surfaces to those of the first and second femoral plateau members 150, 160 and are constructed to mate in a complementary manner with the condyles 12, 14 of the femur 10. Alternatively, the spacer blocks can have different shaped surfaces, such as flat planes so that they can fit the femur 10 after the distal femoral and posterior femoral cuts are made. By measuring the gap spaces between the femur 10 and tibia 20, the physician can determine if the required distraction height is greater than the maximum height achievable by the distraction device 100. The system can also advise the surgeon as to which height of spacer block to use in order to sufficiently augment the distraction height, while keeping the distraction device's dynamic range of motion or workspace in a suitable location.

The height of each of the first and second upper femoral plateau members 150, 160 is preferably independently controlled by a controller or some other type of mechanism. There are any number of different techniques that can be used to control the movement of the first and second upper femoral plateau members 150, 160 relative to the first and second base plates 120, 130. For example, the height can be controlled by a hydraulic system. Since the height of the distraction device 100 can be readily changed, the portion of the device 100 that is inserted into the joint can remain as small as possible, and require only a minimum opening of the joint.

FIG. 4 illustrates one exemplary means 300 for controlling the height of the first and second upper femoral plateau members 150, 160 relative to the first and second base plates 120, 130. The illustrated means 300 is a fluid based system and includes a first fluid holding member that is expandable (first pouch) 310 that is intended to be associated with one of the linkage mechanisms 200 and a second fluid holding member that is expandable (second pouch) 320 that is intended to be associated with another linkage mechanism 200. More specifically, the first pouch 310 is constructed to surround one linkage mechanism 200 and receive and hold a fluid (e.g., water) and the second pouch 320 is constructed to surround another linkage mechanism 200. The first pouch 310 is thus a flexible member that has a hollow interior 310 that is constructed to accommodate the linkage mechanisms 200 which in the illustrated embodiments is defined by three pairs of links pairs.

Each of the first and second pouches 310, 320 has an upper part 312 and an opposing lower part 314, with the upper part 312 being coupled to a first intermediate plate 330, while the lower part 314 is coupled to a second intermediate plate 340. The intermediate plates 330, 340 can have any number of different sizes and shapes so long as they are complementary to the other parts and perform the function of providing a mounting surface or substrate that permits the linkage mechanism 200 to be mounted between the base 110 and the upper femoral plateau members 150, 160. In the illustrated embodiment, the intermediate plates 330, 340 are in the form of disks or the like.

In fact, the linkage pairs defined by parts 210, 220 are disposed between the two intermediate plates 330, 340, with the part 210 being attached to the first intermediate plate 330 and the part 220 being attached to the second intermediate plate 340.

The upper part 312 of the first pouch 310 can be coupled to the first intermediate plate 330 with fastening means 332 (such as screws or the like) and the lower part 314 can be coupled to the second intermediate plate 340 with fastening means 332, with the plates 330, 340 being attached to the first upper femoral plateau member 150 and the base plate 120. Similarly, the upper part 312 of the second pouch 320 can be coupled to the first intermediate plate 330 with fastening means 332 (such as screws or the like) and the lower part 314 can be coupled to the second intermediate plate 340 with fastening means 332, with the plates 330, 340 being attached to the second upper femoral plateau member 160 and the base plate 130. The attachment of the first and second pouches 310, 320 to the intermediate plates 330, 340 forms a tight waterproof seal.

Openings 350 formed in the linkage mechanisms 200 prevent hole bosses 352 from interfering and impinging upon the links 210, 220 through the course of the range of distractor motion. In other words, as the distraction device 100 moves over its range of motion (up and down) the screw bosses 352 will likewise move; however, the openings 350 are formed in the links 210, 220 to permit reception of the screw bosses 352 and therefore, permit smooth movement of the device 100.

The pouches 310, 320 can be made out of a medical grade plastic or PVC or any other suitable material. Preferably, the pouches 310, 320 are made from a material that is the least extensible as possible so that the distraction height does not change significantly when loads are applied. The material should be bendable to accommodate changes in the shape as the plateau height is increased or decreased, but should also resist expanding or stretching like a balloon when the fluid pressure increases. In other words, if the fluid volume in the pouches 310, 320 is held constant, the distraction height should also remain constant even if the loads are applied since the pouches 310, 320 do not expand under the applied pressure.

The pouches 310, 320 can be manufactured as two separate discs and joined together around the linkage mechanisms 200 with a seam to reduce manufacturing costs. Preferably, the seam is made using a high frequency welding machine so as to be strong and resist rupturing.

In one embodiment, the pouches 310, 320 are fluid operated with fluid being supplied by means of conduits (tubes) 360 that can extend from the pouches 310, 320 to transmit the fluid. The conduits 360 can be flexible so as not to interfere with the patella and the tissues surrounding the joint as the knee joint is flexed and distracted. The fluid can be sterile water, saline solution, mineral oil, or any other appropriate fluid. A purge system can be incorporated to remove any bubbles in the system.

The height of each of the first and second upper femoral plateau members 150, 160 is independently controlled by a controller or the like. The controller can include one or more motors or the like that are operated to control the amount of fluid in each pouch 310, 320 and the height of the respective first and second upper femoral plateau members 150, 160. Operation of the motors results in fluid traveling through the conduits 360 into the pouches 310, 320 and this causes the fluid pressure to increase in the pouch 310, 320. Apposing forces are applied to the intermediate plates 330, 340 resulting in an increase in height of the upper femoral plateau plate 150, 160 relative to the base plates 120, 130 (first and second degrees of freedom (DOF)). This in turn causes the position of the femur 10 to change relative to the tibia 20 in the knee joint.

It will be appreciated that any number of different types of controllers, actuators, devices, etc., can be used to cause a controlled change in the distraction device 100.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different claims set forth below may be combined in various ways in further accordance with the present invention.

What is claimed is:

1. A medical instrument comprising:
    a base;
    an upper member; and
    a linkage mechanism that is a separate structure relative to the base and, upper member and is coupled to the base and the upper member and being operable to maintain the upper member in a variable fixed position that is substantially parallel to the base and spaced a predetermined, variable distance therefrom, wherein the linkage mechanism includes at least two link pairs, each link pair having a first link that is pivotally coupled to the upper member and a second link that is pivotally coupled to the base, the first and second links being pivotally coupled to one another about a pivot axis, the at least two link pairs being arranged at an angle relative to one another such that the pivot axes of the at least two link pairs are oriented in a non-parallel manner resulting in that when one link pair opens, the other link pair opens at an equal angle resulting in the upper member being constrained to remain parallel to the base.

2. The instrument of claim 1, wherein the base includes a first base plate and a second base plate that is pivotably coupled to the first base plate, wherein at least a portion of the first and second base plates lie in the same plane.

3. The instrument of claim 2, wherein each of the base plates includes a main portion and a raised portion connected thereto by an inclined portion, the main portions of the first and second base plates lying in the same first plane, the raised portions of the first and second base plates lie in the same second plane that is parallel to the first plane.

4. The instrument of claim 3, wherein the first and second base plates are pivotally connected to one another by a pivot joint that is formed in the raised portions of the first and second base plates.

5. The instrument of claim 1, wherein the upper member has an upper surface configured to support a mass.

6. The instrument of claim 5, wherein the upper surface has a concave shape and the mass comprises a bone.

7. The instrument of claim 1, wherein the device is a knee distraction device and is formed of a pair of base plates and the upper member is formed of a pair of upper femoral plateau members for supporting condyles of a femur.

8. The instrument of claim 1, further including a controller operably coupled to the linkage mechanism to cause the controlled movement thereof resulting in movement of the upper member relative to the base.

9. The instrument of claim 8, wherein the controller is operably connected to an adjustable spacer element that has a body disposed around the linkage mechanism, the body being fluidly connected to a fluid source such that controlled delivery of fluid to the body results in expansion of the spacer element and a distance between the upper part and base increasing, wherein expansion of the spacer element causes opening of the linkage mechanism.

10. The instrument of claim 9, wherein the body of the spacer element comprises an expandable pouch that has a hollow interior in which the linkage mechanism is disposed, the pouch being secured to the upper member and the base by means of fastening elements.

11. The instrument of claim 10, wherein the linkage mechanism includes openings formed therein to receive the fastening elements to accommodate movement of the linkage mechanism and the pouch over a range of motion for the device.

12. The instrument of claim 1, wherein the linkage mechanism comprises three link pairs arranged such that the pivot axes thereof are arranged in a non-parallel manner.

13. The instrument of claim 1, further including a pair of intermediate plates with one intermediate plate being securely attached to the upper part and the other intermediate plate being attached to the base, with the linkage mechanism being disposed between the pair of intermediate plates.

14. The instrument of claim 1, wherein a minimum spacing between external surfaces of the upper part and the base being less than 10 millimeters.

15. A distraction device for use in a surgical application to space one bone a predetermined distance from another bone comprising:
    a base;
    an upper member; and
    a linkage mechanism that is a separate structure relative to the base and upper member and is coupled to the base and the upper member and being operable to maintain the upper member in a variable fixed position that is substantially parallel to the base and spaced a predetermined, variable distance therefrom, wherein the linkage mechanism includes at least three link pairs with each link pair having a pivot axis, the pivot axes being arranged at angles relative to one another resulting in the pivot axes intersecting one another such that when one link element opens, the other link elements open with at an equal angle resulting in the upper member being constrained to remain parallel to the base.

16. A distraction device for use in a surgical application to space one bone a predetermined distance from another bone comprising:
    a base that includes a first base plate and a second base plate, wherein each of the base plates includes a first portion and a second portion, the first portions lying in the same first plane, while the second portions lie in the same second plane that is parallel to the first plane, the second portions being pivotally coupled to one another;
    a pair of upper members; and
    a pair of linkage mechanisms, each of which is a separate, removable structure relative to the base and upper member and is coupled to one first portion of the base and one upper member and being operable to maintain the upper member in a variable fixed position that is substantially parallel to the base and spaced a predetermined, variable distance therefrom, wherein the linkage mechanism includes at least two link pairs, each link pair having a first link that is pivotally coupled to the upper member and a second link that is pivotally coupled to the base, the first and second links being pivotally coupled to one another about a pivot axis, the at least two link pairs being arranged at an angle relative to one another such that the pivot axes of the at least two link pairs are oriented in a non-parallel manner resulting in that when one link pair opens, the other link pair opens at an equal angle resulting in the upper member being constrained to remain parallel to the base.

* * * * *